US00PP36461P2

(12) United States Plant Patent
Bentley

(10) Patent No.: US PP36,461 P2
(45) Date of Patent: Feb. 18, 2025

(54) ***ARMERIA* PLANT NAMED 'Hypnotic Dreams'**

(50) Latin Name: *Armeria pseudarmeria*
Varietal Denomination: Hypnotic Dreams

(71) Applicant: Howard Bentley, Wonga Park (AU)

(72) Inventor: Howard Bentley, Wonga Park (AU)

(73) Assignee: PLANT GROWERS AUSTRALIA PTY. LTD., Victoria (AU)

( * ) Notice: Subject to any disclaimer, the term of this patent is extended or adjusted under 35 U.S.C. 154(b) by 0 days.

(21) Appl. No.: 18/907,411

(22) Filed: Oct. 4, 2024

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Armeria* plant named 'Hypnotic Dreams', characterized by its upright, dense and uniformly mounded plant habit; long narrow dark green-colored leaves; freely flowering habit; medium to large inflorescences with numerous purplish red-colored flowers; peduncles that are upright and rigid and good garden performance.

2 Drawing Sheets

Figure 1:
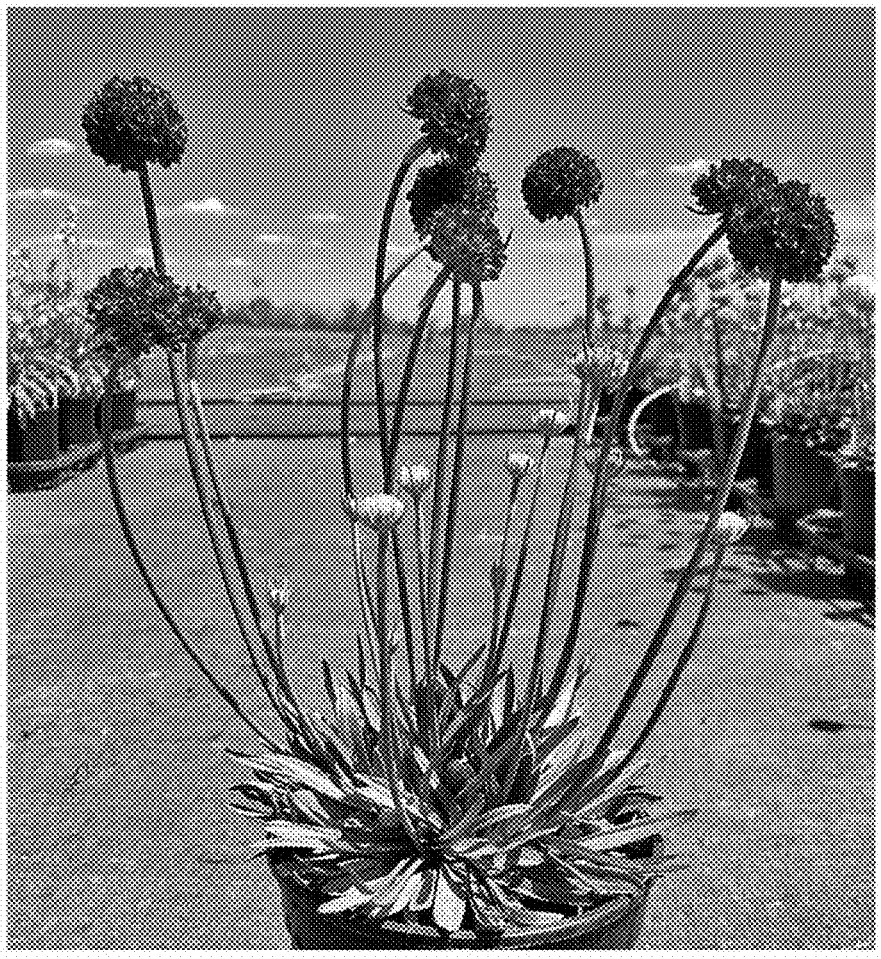

Botanical designation: *Armeria pseudarmeria.*
Cultivar denomination: 'HYPNOTIC DREAMS'.

CROSS-REFERENCED TO CLOSELY-RELATED APPLICATIONS

Title: *Armeria* Plant Named 'Vivid Dreams'
Inventors: Steven Eggleton & Howard Bentley
Disclosed in U.S. Plant Pat. No. 35,236

BACKGROUND OF THE INVENTION

The present invention relates to a new and distinct cultivar of *Armeria* plant, commonly referred to as Thrift or Sea Pinks, botanically known as *Armeria pseudarmeria*, commercially used as a garden plant, and hereinafter referred to by the name 'Hypnotic Dreams'.

The new *Armeria* plant is a product of a planned breeding program conducted by the Inventor in Wonga Park, Victoria, Australia. The objective of the breeding program is to create new *Armeria* plants with uniform, dense and upright plant habit, upright and rigid peduncles, large globular inflorescences, attractive flower color and good garden performance.

The new *Armeria* plant originated from a cross-pollination conducted by the Inventor in Wonga Park, Victoria, Australia in November 2015 of *Armeria pseudarmeria* 'Dream Weaver', disclosed in U.S. Plant Pat. No. 30,600, as the female, or seed, parent with a proprietary selection of *Armeria pseudarmeria* identified as red selection #2, not patented, as the male, or seed, parent. The new *Armeria* plant was discovered and selected by the Inventor as a single flowering plant from within the progeny of the stated cross-pollination grown in a controlled greenhouse environment in Wonga Park, Victoria, Australia in October 2016.

Asexual reproduction of the new *Armeria* plant since October 2016 by vegetative cuttings in a controlled environment in Wonga Park, Victoria, Australia has shown that the unique features of this new *Armeria* plant are stable and reproduced true to type in successive generations.

SUMMARY OF THE INVENTION

Plants of the new *Armeria* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'Hypnotic Dreams'. These characteristics in combination distinguish 'Hypnotic Dreams' as a new and distinct *Armeria* plant:

1. Upright, dense and uniformly mounded plant habit.
2. Long narrow dark green-colored leaves.
3. Freely flowering habit.
4. Medium to large inflorescences with numerous purplish red-colored flowers.
5. Peduncles that are upright and rigid.
6. Good garden performance.

Plants of the new *Armeria* can be compared to plants of the female parent, 'Dream Weaver'. Plants of the new *Armeria* differ primarily from plants of the female parent selection in flower color as plants of the new *Armeria* have purplish red-colored flowers whereas plants of 'Dream Weaver' have deep rose pink-colored flowers.

Plants of the new *Armeria* can be compared to plants of the male parent selection. Plants of the new *Armeria* differ primarily from plants of the male parent selection in flower color as plants of the new *Armeria* have purplish red-colored flowers whereas plants of the male parent selection have red-colored flowers. In addition, plants of the new *Armeria* have shorter and stronger peduncles than plants of the male parent selection.

Plants of the new *Armeria* can be compared to plants of *Armeria pseudarmeria* 'Vivid Dreams', disclosed in U.S.

Plant Pat. No. 35,236. Plants of the new *Armeria* differ primarily from plants of 'Vivid Dreams' in flower color as plants of the new *Armeria* have purplish red-colored flowers whereas plants of 'Vivid Dreams' have strong reddish purple-colored flowers.

Plants of the new *Armeria* can also be compared to plants of *Armeria pseudarmeria* 'Happy Dreams', not patented. Plants of the new *Armeria* differ primarily from plants of 'Happy Dreams' in flower color as plants of the new *Armeria* have purplish red-colored flowers whereas plants of 'Happy Dreams' have red-colored flowers.

BRIEF DESCRIPTION OF THE PHOTOGRAPHS

The accompanying colored photographs illustrate the overall appearance of the new *Armeria* plant showing the colors as true as it is reasonably possible to obtain in colored reproductions of this type. Colors in the photographs may differ slightly from the color values cited in the detailed botanical description which accurately describe the colors of the new *Armeria* plant.

The photograph on the first sheet (FIG. 1) is a side perspective view of a typical flowering plant of 'Hypnotic Dreams' grown in a container.

Figure 2:
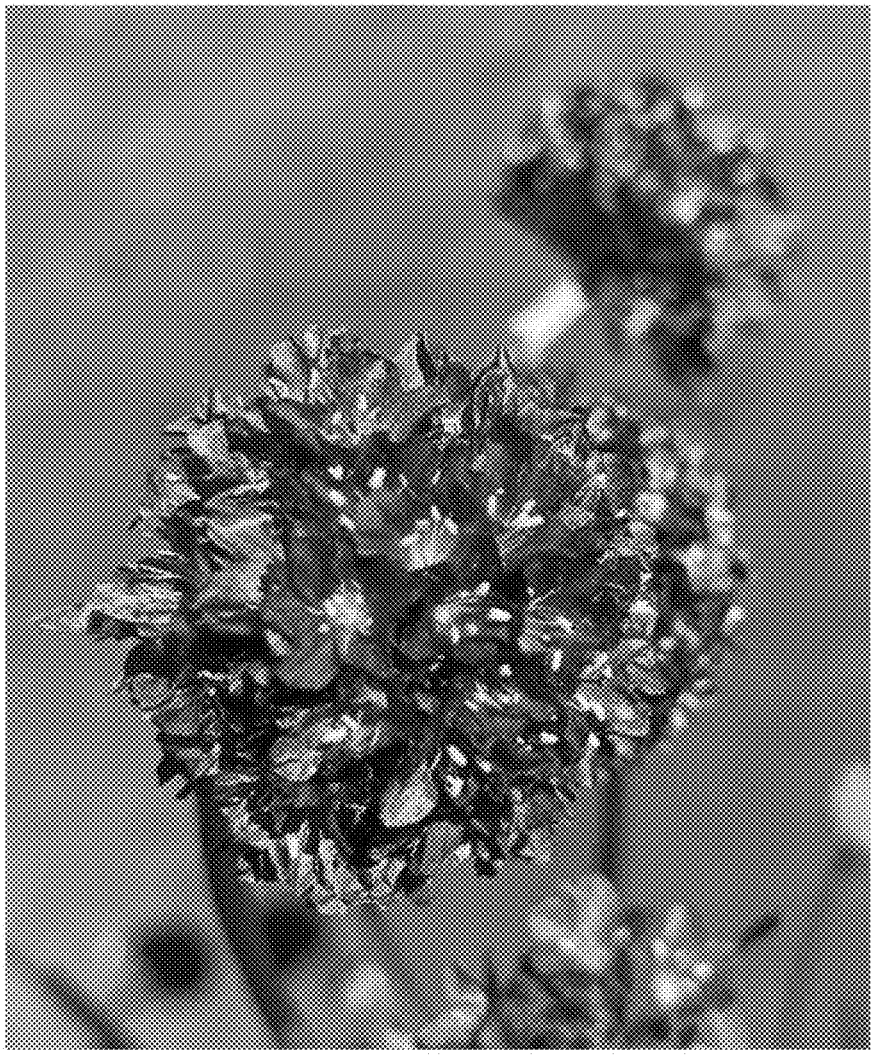

The photograph on the second sheet (FIG. 2) is a close-up view of typical inflorescences of 'Hypnotic Dreams'.

DETAILED BOTANICAL DESCRIPTION

The aforementioned photographs and following observations, measurements and values describe plants grown during the spring in outdoor nurseries in Elburn, Illinois and Fort Worth, Texas and under cultural practices typical of commercial *Armeria* production. During the production of the plants, day temperatures ranged from 32° C. to 40° C. and night temperatures ranged from 21° C. to 35° C. Plants were six months old when the photographs and the description were taken. In the description, color references are made to The Royal Horticultural Society Colour Chart, 2015 Edition, except where general terms of ordinary dictionary significance are used.

Botanical classification: *Armeria pseudarmeria* 'Hypnotic Dreams'.

Parentage:

- *Female, or seed, parent.*—*Armeria pseudarmeria* 'Dream Weaver', disclosed in U.S. Plant Pat. No. 30,600.
- *Male, or pollen, parent.*—Proprietary selection of *Armeria pseudarmeria* identified as red selection #2, not patented.

Propagation:

- *Type.*—By vegetative cuttings.
- *Time to initiate roots, summer.*—About ten days at soil temperatures about 20° C. and ambient temperatures about 25° C.
- *Time to initiate roots, winter.*—About 20 days at soil temperatures about 20° C. and ambient temperatures about 15° C.
- *Time to produce a rooted young plant, summer.*—About 40 days at soil temperatures about 20° C. and ambient temperatures about 25° C.
- *Time to produce a rooted young plant, winter.*—About 60 days at soil temperatures about 12° C. and ambient temperatures about 12° C.
- *Root description.*—Medium thickness, fibrous; typically white in color, actual color of the roots is dependent on substrate composition, water quality, fertilizer type and formulation, substrate temperature and physiological age of roots.
- *Rooting habit.*—Moderately freely branching; medium density.

Plant description:

- *Plant and growth habit.*—Herbaceous perennial typically grown as a landscape plant; plants are dense, upright and uniformly mounded; basally clumping with leaves and flower peduncles developing from the base; freely branching and flowering habit; flowers arranged in dense globular terminal umbels; moderately vigorous growth habit and moderate growth rate.
- *Plant height, soil level to top of foliar plane.*—About 6 cm to 7 cm.
- *Plant height, soil level to top of inflorescences.*—About 28 cm to 30 cm.
- *Plant diameter (spread).*—About 16 cm to 19 cm.

Stem description:

- *Length.*—About 1 cm.
- *Diameter.*—About 5 mm.
- *Strength.*—Strong.
- *Texture and luster.*—Smooth, glabrous; matte.
- *Color.*—Close to 177A.

Leaf description:

- *Arrangement.*—Basal rosette, simple, sessile.
- *Length.*—About 9 cm to 10.5 cm.
- *Width.*—About 5 cm to 5.5 cm.
- *Shape.*—Acicular, carinate.
- *Apex.*—Acute.
- *Base.*—Clasping.
- *Margin.*—Entire; not undulate.
- *Texture and luster, upper surface.*—Smooth, glabrous; moderately glossy.
- *Texture and luster, lower surface.*—Smooth, glabrous; slightly to moderately glossy.
- *Venation pattern.*—Parallel.
- *Color.*—Developing leaves, upper and lower surfaces: Close to 147A. Fully expanded leaves, upper surface: Close to 147A; towards the base, close to NN155D and at the base, close to 60A; venation, close to 147A, proximally, close to NN155D and at the base, close to 60A. Fully expanded leaves, lower surface: Close to 147A; towards the base, close to between NN155D and 157A and at the base, close to 60A; venation, close to 146A, proximally, close to between NN155D and 157A and at the base, close to 60A.

Flower description:

- *Flower arrangement and habit.*—Single salverform to star-shaped tubular flowers arranged in dense terminal umbels; flowers sessile; freely flowering habit with about 75 to 85 flowers developing per inflorescence and numerous inflorescences developing per plant during the flowering season; flowers face upright to outwardly depending on position on the inflorescence; inflorescences hemispherical to almost spherical in overall shape.
- *Fragrance.*—None detected.
- *Flowering response.*—Plants begin flowering about 24 weeks after planting and flower continuously in the garden from early spring to early summer.

*Post-production longevity*.—Flowers last about one to two weeks on the plant depending on temperatures; corolla not persistent, calyx persistent.

*Inflorescence height*.—About 2.4 cm to 2.5 cm.

*Inflorescence diameter*.—About 2.8 cm to 3 cm.

*Flower diameter*.—About 4 mm.

*Flower depth* (*height*).—About 1 cm.

*Flower throat diameter*.—About 1 mm to 1.5 mm.

*Flower tube length*.—About 5 mm to 6 mm.

*Flower tube diameter, proximally*.—About 1 mm.

*Flower buds*.—Length: About 1.5 cm. Diameter: About 5 mm. Shape: Narrowly ovoid. Texture and luster: Smooth, glabrous; slightly glossy Color: Close to 146A.

*Petals*.—Quantity and arrangement: About five, occasionally, six, in a single whorl, fused towards the base. Length: About 5 mm to 6 mm. Width: About 1.5 mm to 2 mm. Shape: Elongated spatulate. Apex: Obtuse to broadly acute. Margin: Entire. Texture and luster, upper and lower surfaces: Smooth, glabrous; slightly glossy. Color: When opening, upper and lower surfaces: Close to 71A and towards the base, close to NN155C. Fully opened, upper and lower surfaces: Close to 71A and towards the base, close to NN155C to NN155D; color does not fade with subsequent development; however at senescence, petals will become brown, close to 176A.

*Sepals*.—Calyx length: About 7 mm to 8 mm. Calyx diameter, distally: About 2.5 mm to 3 mm. Calyx diameter, proximally: About 1.25 mm. Calyx shape: Tubular, distally, sepals flaring outwardly. Quantity and arrangement: Five to seven in a single whorl, lower 75% to 80% fused. Length: About 7 mm to 8 mm. Width, lobe: About 1.25 mm. Shape, lobe: Roughly deltoid. Apex: Long acuminate. Margin: Entire. Texture and luster, upper and lower surfaces: Smooth, glabrous; moderately glossy.

*Involucral bracts, inner whorl*.—Quantity and arrangement: About twelve in a single whorl at the base of the inflorescence. Length: About 8 mm. Width: About 3 mm. Shape: Linear. Apex: Acute. Margin: Entire. Texture and luster, upper and lower surfaces: Smooth, glabrous; semi-glossy. Color, upper surface: Close to between 144A and 146A. Color, lower surface: Close to 146A.

*Involucral bracts, outer whorl*.—Quantity and arrangement: About five to six in a single whorl subtending the inner whorl of involucral bracts. Length: About 1.7 cm to 1.9 cm. Width: About 4 mm to 6 mm. Shape: Linear. Apex: Acute. Margin: Entire. Texture and luster, upper and lower surfaces: Smooth, glabrous; semi-glossy. Color, upper surface: Close to 146A. Color, lower surface: Close to 147A.

*Involucral sheath*.—Quantity and arrangement: One at the base of the inflorescence; downwardly orientated and appressed to the peduncle. Length: About 1.5 cm. Width: About 3 mm to 5 mm. Shape: Tubular. Apex: Jagged, praemorse. Margin: Entire. Texture and luster, inner surface: Smooth, glabrous; papery; slightly glossy. Texture and luster, outer surface: Smooth, glabrous; papery; matte. Color, upper and lower surfaces: Proximally, close to 146A and distally, close to NN155D and translucent.

*Peduncles*.—Length: About 25.5 cm to 27 cm. Diameter: About 3 mm. Aspect: Mostly upright to curving upright. Strength: Strong, rigid and not flexible. Texture and luster: Smooth, glabrous; slightly glossy. Color: Close to 139A.

*Reproductive organs*.—Androecium: Stamen number: Five to seven per flower. Filament length: About 2.5 mm. Filament color: Close to 157C to 157D. Anther length: About 1 mm. Anther shape: Oblong. Anther color: Close to 9D. Amount of pollen: None observed. Gynoecium: Pistil number: One per flower. Pistil length: About 4.25 mm, thread-like. Style length: About 4 mm. Style color: Close to 157C to 157D. Stigma diameter: Less than 1 mm. Stigma shape: Pointed. Stigma color: Close to 157C to 157D. Ovary color: Close to 144A.

*Seeds and fruits*.—To date, seed and fruit development have not been observed on plants of the new *Armeria*.

Pathogen & pest resistance: To date, plants of the new *Armeria* have not been observed to be resistant to pathogens and pests common to *Armeria* plants.

Garden performance: Plants of the new *Armeria* have been observed to have good garden performance and to tolerate wind, rain and temperatures ranging from about 1° C. to about 40° C.

It is claimed:

1. A new and distinct *Armeria* plant named 'Hypnotic Dreams' as herein illustrated and described.

* * * * *